(12) United States Patent
Bharate et al.

(10) Patent No.: US 10,377,781 B2
(45) Date of Patent: Aug. 13, 2019

(54) ALKYLIDENE PHOSPHONATE ESTERS AS P-GLYCOPROTEIN INDUCERS

(71) Applicant: Council of Scientific & Industrial Research, New Delhi (IN)

(72) Inventors: Sandip Bharate, Jammu (IN); Ajay Kumar, Jammu (IN); Sudhakar Manda, Jammu (IN); Prashant Joshi, Jammu (IN); Sonali Bharate, Jammu (IN); Abubakar Wani, Jammu (IN); Sadhana Sharma, Jammu (IN); Ram Vishwakarma, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/510,952

(22) PCT Filed: Sep. 16, 2015

(86) PCT No.: PCT/IN2015/050110
§ 371 (c)(1),
(2) Date: Mar. 13, 2017

(87) PCT Pub. No.: WO2016/063297
PCT Pub. Date: Apr. 28, 2016

(65) Prior Publication Data
US 2017/0275314 A1   Sep. 28, 2017

(30) Foreign Application Priority Data
Oct. 21, 2014 (IN) .......................... 3010/DEL/2014

(51) Int. Cl.
*C07F 9/655* (2006.01)
*C07F 9/40* (2006.01)

(52) U.S. Cl.
CPC .......... *C07F 9/65515* (2013.01); *C07F 9/404* (2013.01); *C07F 9/405* (2013.01); *C07F 9/4031* (2013.01); *C07F 9/4034* (2013.01); *C07F 9/4037* (2013.01)

(58) Field of Classification Search
CPC .... C07F 9/4031; C07F 9/4034; C07F 9/4037; C07F 9/404; C07F 9/405; C07F 9/65515
See application file for complete search history.

(56) References Cited

U.S. PATENT DOCUMENTS

| | | | | |
|---|---|---|---|---|
| 5,128,331 A | * | 7/1992 | Nguyen | C07F 9/386 514/101 |
| 6,127,350 A | * | 10/2000 | Niesor | A61K 31/663 514/107 |
| 2002/0022599 A1 | | 2/2002 | Synold et al. | |
| 2004/0190027 A1 | | 9/2004 | Foster et al. | |
| 2006/0269496 A1 | | 11/2006 | Hwang | |

FOREIGN PATENT DOCUMENTS

| | | | |
|---|---|---|---|
| CA | 2 28 974 A1 | 7/2011 | |
| DE | 197 38 005 A1 * | 3/1999 | ............... C07F 9/38 |
| WO | 97/04785 A1 | 2/1997 | |
| WO | 99/48915 A1 | 9/1999 | |
| WO | 01/72837 A2 | 4/2001 | |
| WO | 02/11704 A2 | 2/2002 | |
| WO | 03/094851 A2 | 11/2003 | |
| WO | 2009/026428 A1 | 2/2009 | |
| WO | 2011/085293 A1 | 7/2011 | |

OTHER PUBLICATIONS

McInerney et al., "Development and validation of an in-cell western for quatifying P-glycoprotein expression in human brain microvascular endothelial (hCMEC/D3) cells", Journal of Pharmaceutical Sciences, pp. 1-27.
Newman et al., "Assessing the impact of lithium chloride on the expression of P-glycoprotein at the blood-brain barrier", Journal of Pharmaceutical Sciences, pp. 1-25.
Bharate et al., "Design, synthesis and p-gp induction activity of aryl phosphonate esters: Identification of tetraethyl-2-phenylethene-1,1-diyldiphosphonate as an orally bioavailable P-gp inducer", MedChemComm, pp. 1-7.
Lecercle et al., "Phosphine-Catalyzed .alpha.-P-Addition on Activated Alkynes: A New Route to P-C-P Backbones", Database Accession No. 2006:844257, Abstract, Organic Letters (2006), 8(19), 4283-4285, XP-002752574.
(Continued)

*Primary Examiner* — Joseph R Kosack
(74) *Attorney, Agent, or Firm* — Nixon Peabody LLP; Jeffrey L. Costellia

(57) ABSTRACT

The present invention relates to the alkylidene phosphonate esters of formula I wherein, $R_1$ is selected from a group consisting of hydrogen or alkyl group; $R_2$ is selected from a group consisting of hydrogen, hydroxy, alkyl, alkoxy, nitro, halogen, amino, N-substituted alkylamino; alkyl group is selected from a group consisting of methyl, ethyl and isopropyl; Ar is selected from a group consisting of aryl, substituted aryl, fused aryl, heteroaryl, and substituted heteroaryl. The present invention particularly relates to synthesis and p-glycoprotein induction activity of the alkylidene phosphonate esters. In addition, the invention relates to methods of using compounds for treating or preventing Alzheimer's disease.

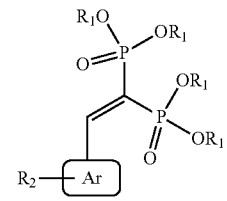

8 Claims, 3 Drawing Sheets

(56) References Cited

OTHER PUBLICATIONS

Heuclin et al, "Phosphorus stabilized carbene complexes: bisphosphonate dianion synthesis, reactivity and DFT studies of O.apprx.C.apprx.O zirconium(IV) complexes", Database Accession No. 2009:1564281, Abstract, Dalton Transactions (2010), 39(2), 492-499, XP-002752575.
Xue et al, "A Facile Cu(I)/TF-BiphamPhos-Catalyzed Asymmetric Approach to Unnatural .alpha-Amino Acid Derivatives Containing gem-Bisphosphonates", Database Accession No. 2011:883243, Abstract, Journal of the American Chemical Society (2011), 133(30), 11757-11765, XP-002752576.
Fotsing et al, "Dioxirane Oxidation of 2-Aryl-1-vinyl-1,1-diphosphane Dioxide: A Convenient Approach for the Synthesis of Novel 1,2-Epoxy-2-aryl Ethylgembisphosphonates", Database Accession No. 2013:503857, Abstract, Heteroatom Chemistry (2013), 24(3), 234-241, XP-002752577.
Wang et al, "Cu(I)/TF-BiphamPhos Catalyzed Reactions of Alkylidene Bisphosphates and Alkylidene Malonates with Azomethine Ylides: Michael Addition versus 1,3-Dipolar Cycloaddition", Database Accession No. 2012:1282307, Abstract, Organometallics (2012), 31(22), 7870-7876, XP-002752578.
Ebetino et al, "Pharmaceutical compositions containing quaternary nitrogen-containing phosphonate for prevention and treatment of abnormal calcium and phosphate metabolism", Database Accession No. 1995:580677 Abstract, Procter and Gamble Pharmaceuticals, Inc., USA, and U.S. Pat. No. 5,391,743, Feb. 21, 1995, XP-002752579.
Bocan, "Prevention of plaque rupture by ACAT inhibitors", Database Accession No. 2001:359777, Abstract, and PCT International Publication No. WO01/34127, May 17, 2001, XP-002752580.
Lehnert, "Knoevenagel condensations with titanium tetrachloride-base. IV. Condensation of aldehydes and ketones with phosphonoacetate and methylenediphosphonates", Database Accession No. 1974:463726, Abstract, Tetrahedron (1974), 30(2), 301-5, XP-002752581.
Moskvin et al, "Spectra, structure and alkaline hydrolysis of arylidenemethanediphosphonic acid esters and their carbo analogs", Database Accession No. 1985:149357, Abstract, Zhurnal Obshchei Khimii (1984), 54(10), 2223-37, XP-002752582.
International Search Report for International Application No. PCT/IN2015/050110, dated Jan. 13, 2016, 6 pages.
Written Opinion of the International Searching Authority for International Application No. PCT/IN2015/050110, dated Jan. 13, 2016, 10 pages.
Response to the Written Opinion of the International Searching Authority for International Application No. PCT/IN2015/050110, dated Mar. 7, 2016, 2 pages.
Mawuenyega, K. G. et al., "Decreased Clearance of CNS β-Amyloid in Alzheimer's Disease," Science, vol. 330, p. 1774-.
Cirrito, J. R. et al., "P-glycoprotein deficiency at the blood-brain barrier increases amyloid-β deposition in an Alzheimer disease mouse model;" Journal of Clinical Investigation, vol. 115, No. 11, pp. 3285-3290 (2005).
Lam, F. C. et al., "β-Amyloid efflux mediate by p-glycoprotein," Journal of Neurochemistry, vol. 76, pp. 1121-1128 (2001).
Berkhout, T. A et al., "The Novel Cholesterol-lowering Drug SR-12813 Inhibits Cholesterol Synthesis via an Increased Degradation of 3-Hydroxy-3-,methylglutaryl-coenzyme A Reductase." The Journal of Biological Chemistry, vol. 271, No. 24, pp. 14376-14382 (1996).
Watkins, R. E. et al., "The Human Nuclear Xenobiotic Receptor PXR: Structural Determinants of Directed Promiscuity," Science, vol. 292, pp. 2329-2333 (2001).
Jones, S.A. et al., "The Pregnane X Receptor: A Promiscuous Xenobitic Receptor That Has Diverged during Evolution," Molecular Endocrinology, vol. 14, No. 1, pp. 27-39 (2000).
Watkins, R.E.et al., "Coactivator Binding Promotes the Specific Interaction Between Ligand and the Pregame X Receptor," J. Mol. Biol., vol. 331, pp. 815-828, (2003).

\* cited by examiner

ALKYLIDENE PHOSPHONATE ESTERS AS P-GLYCOPROTEIN INDUCERS

FIELD OF THE INVENTION

The present invention relates to the alkylidene phosphonate esters. The present invention particularly relates to synthesis and p-glycoprotein induction activity of phosphonate ester class of compounds. The present invention also relates to methods for the treatment of Alzheimer's disease, including those caused by deposition of amyloid-β plaques inside nerve cells. Compounds of the invention can be used for prevention or in the treatment of Alzheimer's disease.

BACKGROUND OF THE INVENTION

Alzheimer's disease is the most common form of senile dementia and the fourth highest cause of disability and death in the elderly. It is characterized by the presence of three main brain hallmarks viz. diffuse neuronal loss with a particular involvement of the cholinergic system, extracellular protein deposits (amyloid plaques) and intracellular protein deposits (neurofibrillary tangles, NFTs). All current therapies are based on the cholinergic hypothesis and demonstrate only symptomatic treatment. Progression of the disease is not slowed or halted, with symptoms continuing to deteriorate over time. The amyloid hypothesis proposes that Alzheimer's disease is caused by an imbalance between Aβ production and clearance, resulting in increased amounts of Aβ in various forms such as monomers, oligomers, insoluble fibrils and plaques in the CNS. The rate of Aβ production is same as that in healthy volunteers; whereas rate of clearance is impaired by 25-30%. High levels of Aβ then initiate cascade of events culminating in neuronal damage and death manifesting as progressive dementia of the Alzheimer's disease type. Evidence shows that insufficient clearance of the Aβ protein is a prime cause in over 95% of Alzheimer's disease patients (Mawuenyega, K. G. et al. *Science* 2010, 330, 1774). Further, it is known that Aβ efflux is mediated by p-glycoprotein efflux pump. The p-glycoprotein deficiency at the blood brain barrier increases Aβ deposition in an Alzheimer's disease (Cirrito, J. R. et al., *J. Clin. Invest.* 2005, 115, 3285). P-glycoprotein (Pgp) is highly expressed on the luminal surface of brain capillary endothelial cells and contributes to the blood brain barrier. There is a direct link between Pgp and Aβ metabolism in vivo. The Pgp activity at the blood brain barrier could affect risk for developing Alzheimer's disease as well as provide a novel diagnostic and therapeutic target (Lam, F. C. et al., *J. Neurochem.* 2001, 76, 1121). Thus, it is evident that drugs that have ability to increase levels of Pgp should increase amyloid-β clearance. The present invention reports identification of new Pgp inducers, showing efficacy at low nanomolar concentrations, and thus have potential to emerge as a treatment for Alzheimer's disease.

SR-12813 [tetra-ethyl 2-(3,5-di-tert-butyl-4-hydroxyphenyl)ethenyl-1,1-bisphosphonate, 1a] is a bisphosphonate ester possessing in-vitro as well as in-vivo cholesterol lowering activity. It lowers cholesterol by increasing the degradation of the HMG-Co A (3-hydroxy-3-methylglutaryl-coenzyme A) reductase enzyme (Berkhout, T. A et al., *J. Biol. Chem.* 1996, 271, 14376-14382) which is a key component of the fatty acid and cholesterol biosynthesis pathway. In HepG2 (hepatocellular carcinoma) cells, SR-12813 reduces the activity of the HMG-Co A reductase with $IC_{50}$ value of 0.85 μM. In-vivo, it causes overexpression of LDL (low-density lipoprotein) receptor mediated LDL uptake which explains its anti-hypocholesterolemic effects (Watkins, R. E. et al., *Science* 2001, 292, 2329-2333).

SR12813 (1a) is a very potent and efficacious activator of both human and rabbit PXR, with $EC_{50}$ values of approximately 200 nM and 700 nM, respectively (Jones, S. A. et al., *Mol. Endocrinol.* 2000, 14, 27-39). SR12813 has been reported to increase CYP3A4 protein levels in rat hepatocytes. In the absence of nuclear receptor regulatory domain SRC-1 (steroid receptor co-activator-1), SR12813 binds at multiple orientations to PXR, whereas in the presence of SRC1, the binding occurs in a fixed orientation. By contrast, SR12813 is very weak activator of rat and mouse PXR (Watkins, R. E. et al., *J. Mol. Biol.* 2003, 331, 815-828). Apart from this, SR12813 has also been reported in treatment of bone diseases (WO2002011704, WO0211704A2), activation of orphan nuclear receptors (WO9948915A1), SXR modulation (WO0172837A2), as antineoplastic agent (WO9704785A1), reduction of hair growth (US2006269496A1), for migraine headaches (WO2011085293A1, CA2823974), induction of CYP3A4 & CYP2C8 (US20020022599), treatment of metabolic disorders caused by the sterol 17-hydroxylase (CYP27) deficiency like cerebrotendinous xanthomatosis, tendon xanthomos (US-200400190027), and as chemopreventive agent in fibrosis caused by radiation treatment (WO2009026428) showed promising Pgp induction activity in LS-180 cells.

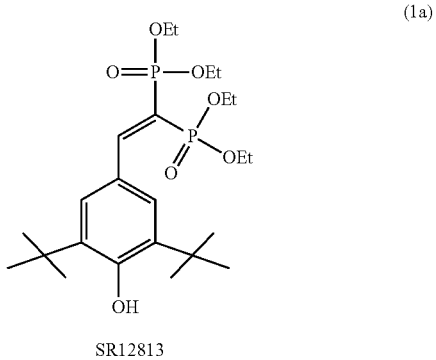 [SMILES: CCOP(=O)(OCC)C(=Cc1cc(C(C)(C)C)c(O)c(C(C)(C)C)c1)P(=O)(OCC)OCC]

(1a)

SR12813

There arises a need to identify new Pgp inducers, showing efficacy at low nanomolar concentrations, and thus have potential to emerge as a treatment for Alzheimer's disease. Therefore, the present invention provides stable compounds which show Pgp induction at low nanomolar concentrations, showed optimal water solubility.

OBJECTIVES OF THE INVENTION

The main object of the invention is to provide phosphonate esters as P-glycoprotein inducers.

Another objective of the invention is to provide the compounds for the treatment of Alzheimer's disease with higher efficacy.

SUMMARY OF THE INVENTION

Accordingly the present invention provides a compound represented by the formula I,

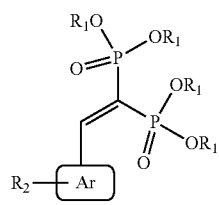

I wherein, $R_1$ is selected from a group consisting of hydrogen or alkyl group; $R_2$ is selected from a group consisting of hydrogen, alkyl, alkoxy, nitro, halogen, amino, N-substituted alkylamino; alkyl group is selected from a group consisting of methyl, ethyl and isopropyl; Ar is selected from a group consisting of aryl, substituted aryl, fused aryl, heteroaryl, and substituted heteroaryl, wherein the substitution in substituted aryl or substituted heteroaryl is with alkoxy group, nitro or N,N-dimethyl amino group.

In an embodiment of the invention, wherein representative compounds comprising the structural formulae:

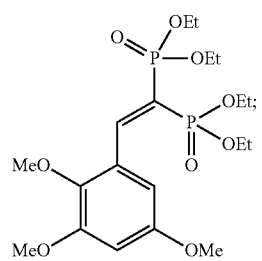

1b

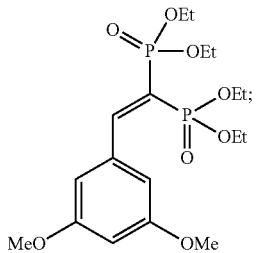

1c

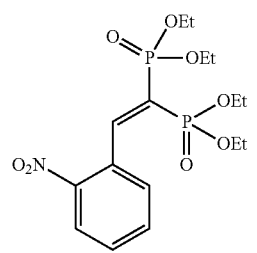

1d

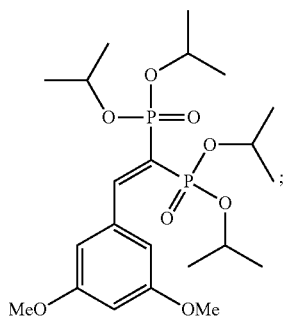

1e

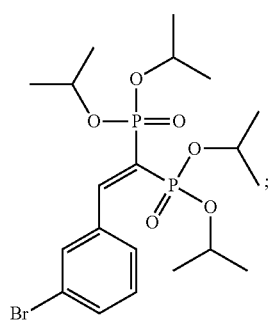

1f

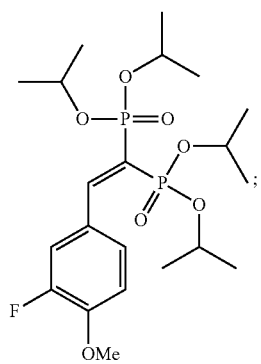

1g

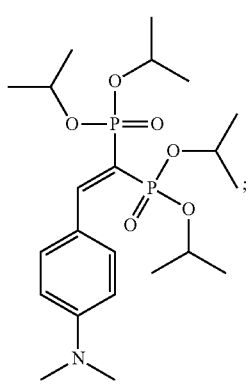

1h

-continued

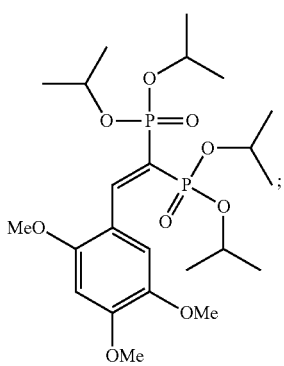

1i

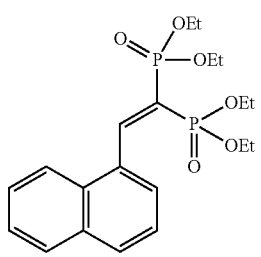

1j

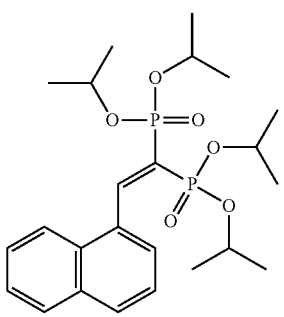

1k

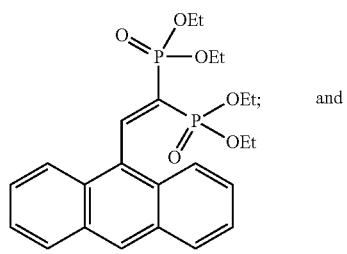

1l and

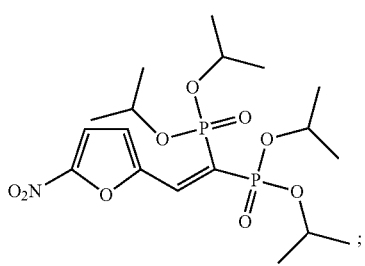

1m

In another embodiment of the invention, wherein the said compounds are useful for the treatment of Alzheimer's disease.

In one more embodiment of the invention, wherein compound 11 displayed $EC_{50}$ of 0.90 nM.

Accordingly the present invention also provides a process for preparation of compound of formula I, wherein the process comprising the steps of;

a. reacting a tetra-alkyl methylenediphosphonate with an aldehyde in $CCl_4$ in presence of $TiCl_4$ and 4-methylmorpholine in THF at a temperature ranging between 0° C. to 35 ° C. for over a period ranging between 10 to 12 hours under stirring, b. quenching the reaction mixture with water and extracting the desired compound with ethyl acetate followed by purification to provide the corresponding alkylidene bisphosphonates.

In an embodiment of the invention wherein the tetraalkyl methylenediphosphonate is selected from a group consisting of tetramethyl methylenediphosphonate, tetraethyl methylenediphosphonate and tetraisopropyl methylenediphosphonates.

In another embodiment of the invention, wherein the aldehyde is having the formula:

Formula II wherein R2 is selected from a group consisting of hydrogen, alkyl, alkoxy, nitro, halogen, amino, N-substituted alkylamino; alkyl group is selected from a group consisting of methyl, ethyl and isopropyl; and Ar is selected from a group consisting of aryl, substituted aryl, fused aryl, heteroaryl, and substituted heteroaryl, wherein the substitution is with an alkoxy, nitro or N,N-dimethyl group.

In another embodiment of the invention is described wherein a pharmaceutical composition for the treatment of Alzheimer's disease comprising; an effective amount of the compound of general formulae I optionally along with the pharmaceutically acceptable excipients, diluents.

In an embodiment of the invention wherein the pharmaceutically acceptable excipient is selected from a group consisting of saccharides (such as lactose, starch, dextrose), stearates (such as stearic acid, magnesium stearate), polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates (such as sodium carbonate, sodium bicarbonate), talc.

LIST OF ABBREVIATIONS

Aβ; Amyloid-β, CNS; Central nervous system, HMG-CoA; 3-hydroxy-3-methylglutaryl-coenzyme A, LDL; Low density lipoprotein, PXR; Pregnane X receptor, SRC-1; Steroid receptor co-activator-1, ANOVA: Analysis of variance; P-gp: P-glycoprotein; Rh123: Rhodamine 123; THF; Tetrahydrofuran, CCl$_4$; Carbon tetrachloride, TiCl4; Titanium tetrachloride.

DETAILED DESCRIPTION OF THE INVENTION

The present invention reports phosphonate esters represented by general structure I as potent Pgp inducer.

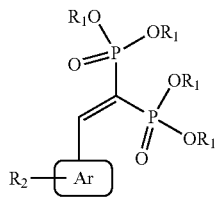

I

Figure 2:
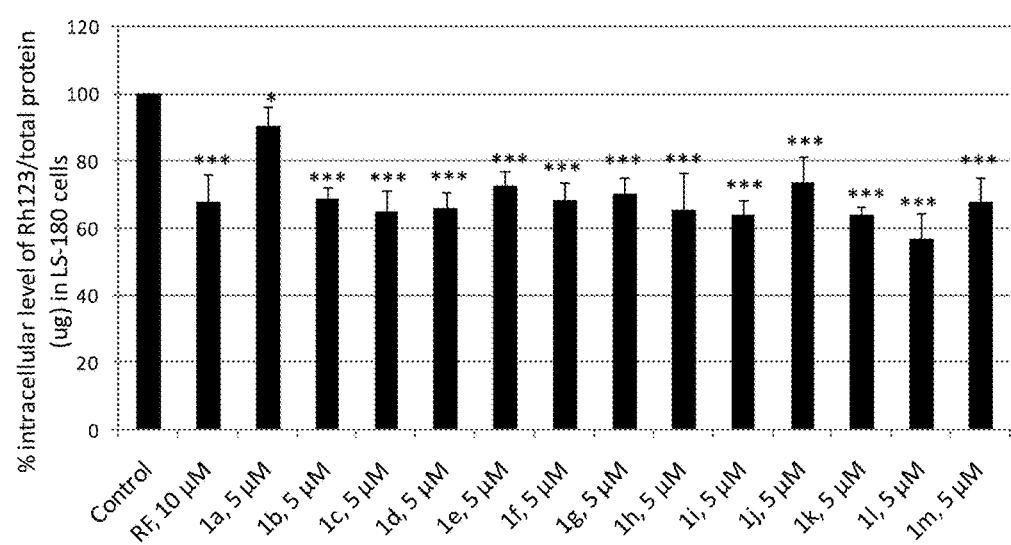
FIG. 2 is a diagram illustrating the Pgp induction activity of phosphonate esters 1a-m, measured in terms of the % intracellular accumulation of rhodamine 123/total protein inside LS180 cells. The decrease in the % intracellular accumulation (compared to control) of Rh123 indicates induction of Pgp. Rifampicin (10 μM) was used as a reference Pgp inducer. Statistical comparisons were made between control vs compounds by using Bonferroni test. The p value <0.5 was considered to be significant. P value *<0.5, <0.01, *<0.001.
Figure 3:
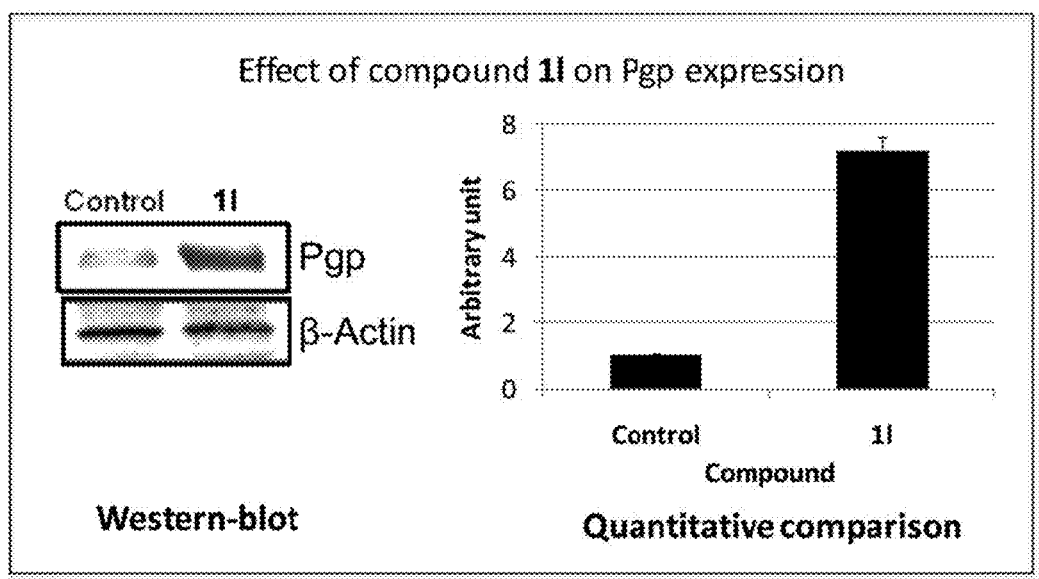
FIG. 3. Pgp Western-blot analysis of phosphonate ester 11. The quantitative comparison of Pgp expression is also shown.

The present invention relates to new phosphonate ester compounds (synthesis shown in FIG. 1) that shows promising p-glycoprotein inducing activity. The bis-phosphonate esters 1b-m showed ability to induce p-glycoprotein as showed by decrease in the % intracellular levels of rhodamine 123 in LS-180 cells (FIG. 2). The compound 11 showed promising induction of p-glycoprotein which was further confirmed by western-blot analysis. The Western-blot results (FIG. 3) clearly indicated that new phosphonate ester 11 induces p-glycoprotein expression. The phosphonate ester 11 showed better Pgp induction activity (EC$_{50}$=0.9 nM) as compared to SR12813 (1a). The compound 11 possesses 2-fold higher EC$_{50}$ value than SR12813 (1a). The EC$_{50}$ results are shown in Table 2. Furthermore, the phosphonate ester 11 also showed optimal solubility in water as well as in biological fluids. The solubility results are shown in Table 3.

A class of phosphonate esters is presented and defined by structural formula I:

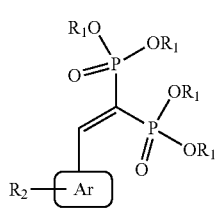

I wherein, R$_1$ is selected from hydrogen and alkyl. Ar is selected from aryl, substituted aryl, fused aryl (for example naphthalene and anthracene), heteroaryl, and substituted heteroaryl. R$_2$ is selected from alkyl, alkoxy, nitro, halogen, amino, N-substituted amino. Alkyl group is selected from methyl, ethyl and isopropyl. The substituted aryl or substituted hetoroaryl groups are substituted with alkoxy group such as methoxy or ethoxy group, nitro or N,N-dimethyl amino group.

Compounds of the invention derived from formula I include, but are not limited to, the following chemical structures:

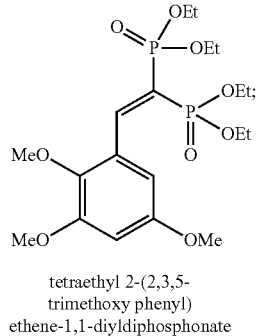

tetraethyl 2-(2,3,5-trimethoxy phenyl) ethene-1,1-diyldiphosphonate (1b)

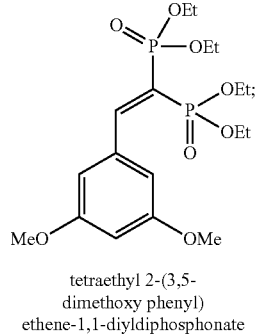

tetraethyl 2-(3,5-dimethoxy phenyl) ethene-1,1-diyldiphosphonate (1c)

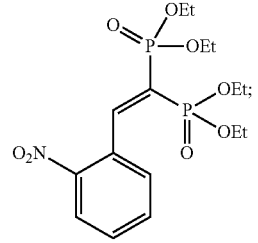

tetraethyl 2-(2-nitrophenyl)-ethene-1,1-diyldiphosphonate (1d)

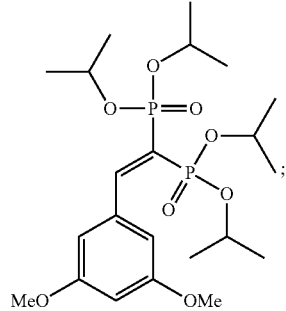

tetraisopropyl 2-(3,5-dimethoxy phenyl) ethene-1,1-diyldiphosphonate (1e)

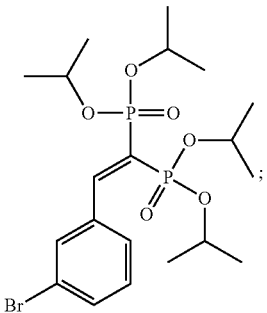

tetraisopropyl 2-(3-bromo phenyl) ethene-1,1-diyldiphosphonate (1f)

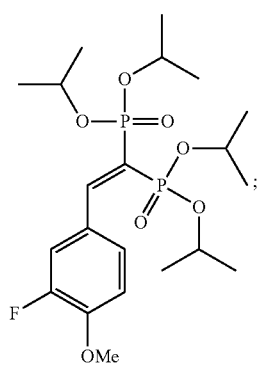

tetraisopropyl 2-(3-fluoro 4-methoxy phenyl) ethene-1,1-diyldiphosphonate (1g)

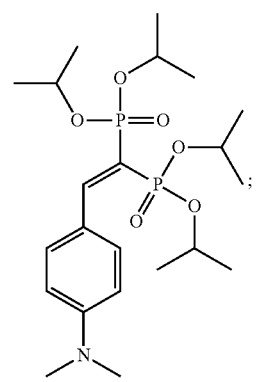

tetraisopropyl 2-(4-N,N-dimethylamino phenyl)-ethene-1,1-diyldiphosphonate (1h)

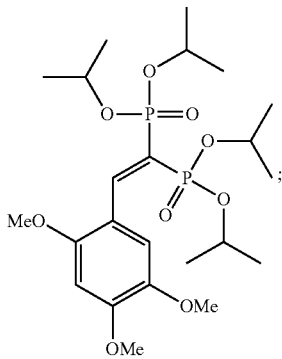

tetraisopropyl 2-(2,4,5-trimethoxy phenyl) ethene-1,1-diyldiphosphonate (1i)

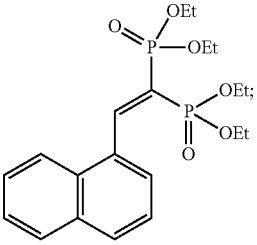

tetraethyl 2-(naphthalen-1-yl)-ethene-1,1-diyldiphosphonate (1j)

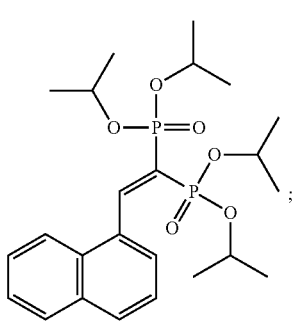

tetraisopropyl 2-(naphthalen-1-yl) ethene-1,1-diyldiphosphonate (1k)

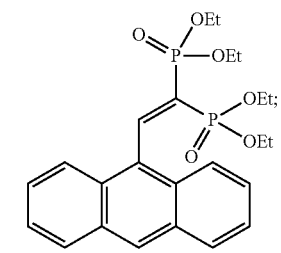

tetraethyl 2-(anthracene-10-yl) ethene-1,1-diyldiphosphonate (1l)

-continued

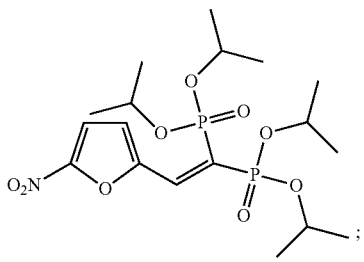

(1m)

tetraisopropyl 2-(4-nitrofuran-2-yl)
ethene-1,1-diyldiphosphonate

As used herein, the terms below have the meanings indicated.

The term "alkyl," as used herein, alone or in combination, refers to a straight-chain or branched-chain alkyl radical optionally substituted containing from 1 to 20 and including 20, preferably 1 to 10, and more preferably 1 to 6, carbon atoms. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "aryl" as used herein, alone or in combination, means a carbocyclic aromatic system containing one, two or three rings wherein such rings may be attached together in a pendent manner or may be fused.

The term "halo," or "halogen," as used herein, alone or in combination, refers to fluorine, chlorine, bromine, or iodine.

The term "alkoxy" as used herein, alone or in combination, refers to oxygen linked 'alkyl' moieties.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The phrase "therapeutically effective" is intended to qualify the amount of active ingredients used in the treatment of a disease or disorder. This amount will achieve the goal of reducing or eliminating the disease or disorder.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

As used herein, the compounds of the invention can be used to treat a patient (e.g. a human) that suffers from or is at a risk of suffering from a disease, disorder, condition, or symptom described herein. The compounds of the invention can be used alone or in combination with appropriate excipients or diluents. Each such treatment described above includes the step of administering to a patient in need thereof a therapeutically effective amount of the compound of the invention described herein to delay, reduce or prevent such a disease, disorder, condition, or symptom.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Following examples are given by way of illustration and should not construed the scope of the present invention.

General procedure for synthesis of alkylidene phosphonate esters 1a-1m. A flame-dried 25 ml round bottom flask with magnetic stir bar was charged with $TiCl_4$ (10 mmol) and 0.5 ml $CCl_4$ at 0° C. Then, 5 ml of dry THF was added dropwise to the flask which resulted in formation of a bright yellow precipitate. Substituted benzaldehyde (5 mmol) and tetraalkyl methylenediphosphonate (5 mmol) were added to the reaction mixture. To this mixture was added dropwise, a solution of 0.5 ml 4-methylmorpholine in 3.0 ml dry THF. The reaction was allowed to warm to room temperature and stirred overnight. The reaction was quenched with water and extracted with EtOAc. The organic layer was washed with brine and dried over $Na_2SO_4$. Concentration in vacuo followed by column chromatography provided the corresponding alkylidene bisphosphonates 1a-1m. In examples 1-13 desired compounds were prepared by the general; procedure as discussed above, wherein the respective aldehydes and tetraalkyl methylenediphosphonates used as reactants to prepare desired compounds are listed in Table 1.

TABLE 1

Starting materials for synthesis of
alkylidene bisphosphonate products

| Substituted benzaldehyde | Tetraalkyl methylenediphosphonate | Alkylidene bisphosphonate product |
|---|---|---|
| 3,5-Di-tert-butyl-4-hydroxybenzaldehyde | Tetraethyl methylenediphosphonate | 1a |
| 2,3,5-Trimethoxybenzaldehyde | Tetraethyl methylenediphosphonate | 1b |
| 3,5-Dimethoxybenzaldehyde | Tetraethyl methylenediphosphonate | 1c |
| 2-Nitrobenzaldehyde | Tetraethyl methylenediphosphonate | 1d |
| 3,5-Dimethoxybenzaldehyde | Tetraisopropyl methylenediphosphonate | 1e |
| 3-Bromobenzaldehyde | Tetraisopropyl methylenediphosphonate | 1f |
| 3-Fluoro-4-methoxybenzaldehyde | Tetraisopropyl methylenediphosphonate | 1g |
| 4-N,N-dimethylamino benzaldehyde | Tetraisopropyl methylenediphosphonate | 1h |
| 2,4,5-Trimethoxybenzaldehyde | Tetraisopropyl methylenediphosphonate | 1i |
| 1-Naphthaldehyde | Tetraethyl methylenediphosphonate | 1j |
| 1-Naphthaldehyde | Tetraisopropyl methylenediphosphonate | 1k |

TABLE 1-continued

Starting materials for synthesis of alkylidene bisphosphonate products

| Substituted benzaldehyde | Tetraalkyl methylenediphosphonate | Alkylidene bisphosphonate product |
|---|---|---|
| Anthracene-9-carbaldehyde | Tetraethyl methylenediphosphonate | 1l |
| 4-Nitrofuraldehyde | Tetraisopropyl methylenediphosphonate | 1m |

Example 1

Tetraethyl-2-(3,5-di-tert-butyl-4hydroxyphenyl)ethane-1,1-diyldiphosphonate(1a)

Yellow oil; yield 60%; $^1$H NMR (400 MHz, CDCl$_3$, ppm): δ8.33-8.14 (dd, $J_1$=28 Hz, $J_2$=48 Hz, 1H), 7.76 (s, 2H), 4.32-4.15 (m, 4H), 4.12-4.02 (m, 4H), 1.46-1.40 (s, 18H), 1.39 1.29 (m, 6H), 1.27-1.16(m, 6H); $^{13}$C NMR (100 MHz, CDCl$_3$, ppm): 6 162.91, 162.88, 157.03, 135.59, 129.87, 125.72, 125.64, 125.51, 125.43, 62.46, 62.41, 62.23, 62.17, 53.42, 34.53, 30.26, 16.39, 16.33, 16.12, 16.04; $^{31}$P NMR (CDCl$_3$, 161.98 MHz; H$_3$PO$_4$ as reference standard): δ19.58-19.26 (d, J=51.83 Hz), 13.62-13.30 (d, J=51.83 Hz); IR (CHCl$_3$): $v_{max}$ 3436, 2957, 2927, 2871, 1616, 1596, 1558, 1424, 1391, 1242, 1162, 1025 cm$^{-1}$; ESI-MS: m/z 505 [M+1]$^+$; HRMS: m/z 505.2468 calcd for C$_{27}$H$_{43}$O$_7$P$_2$+H$^+$ (505.2478).

Example 2

Tetraethyl 2-(2, 3, 5-trimethoxy phenyl)ethene-1,1-diyldiphosphonate (1b)

Yellow oil; yield 50%; $^1$H NMR (400 MHz, CDCl$_3$, ppm): δ8.64-8.44 (dd, $J_1$=28 Hz, $J_2$=48 Hz, 1H), 7.96 (s, 1H), 6.45 (s, 1H), 4.23-4.14 (m, 6H), 4.09-4.02 (m, 2H), 3.94-3.86 (s, 9H), 1.39-1.18 (m, 12H); $^{13}$C NMR (100 MHz, CDCl$_3$, ppm): δ155.98, 154.36, 152.93, 151.42, 142.36, 114.45, 95.39, 62.51, 62.47, 62.40, 62.35, 56.43, 56.34, 56.02, 16.36, 16.31, 16.17; IR (CHCl$_3$): $v_{max}$ 3436, 2927, 1612, 1579, 1508, 1466, 1440, 1335, 1282, 1221, 1128, 1025 cm$^{-1}$; MS: m/z 467.20 [M+Na]$^+$; HRMS: m/z 467.1596 calcd for C$_{19}$H$_{33}$O$_9$P$_2$+H$^+$ (467.1594).

Example 3

Tetraethyl 2-(3,5 dimethoxy phenyl)ethene-1,1-diyldiphosphonate (1c)

Yellow oil; yield: 45%; $^1$HNMR (400 MHz, CDCl$_3$, ppm): δ8.34-8.14 (dd, $J_1$=32 Hz, $J_2$=48 Hz, 1H), 6.99 (d, J=8 Hz, 2H), 6.51 (t, J=4 Hz, 1H), 4.25-4.16 (m, 4H), 4.08-3.97 (m, 4H), 3.81 (s, 6H), 1.43-1.33 (m, 6H), 1.22-1.15 (s, 6H); IR (CHCl$_3$): $v_{max}$ 3436, 2981, 2928, 1586, 1568, 1445, 1391, 1248, 1163, 1025 cm$^{-1}$; ESI-MS: m/z 437.00 [M+1]$^+$; HRMS: m/z 459.1308 calcd for C$_{18}$H$_{30}$O$_8$P$_2$+Na$^+$ (459.1308).

Example 4

Tetraethyl 2-(2-nitrophenyl) ethene-1,1-diyldiphosphonate (1d)

Yellow oil; yield 50%; $^1$H NMR (400 MHz, CDCl$_3$, ppm): δ8.24-8.22 (dd, $J_1$=28 Hz, $J_2$=48 Hz, 1H), 8.24-8.16 (m, 1H), 7.72-7.63 (m, 1H), 7.58-7.50 (m, 2H), 4.32-4.11 (m, 4H), 4.02-3.81 (m, 4H), 1.43-1.36 (m, 6H), 1.15-1.09 (m, 6H); $^{13}$C NMR (100 MHz, CDCl$_3$, ppm): δ159.04, 145.39, 133.59, 130.64, 129.74, 124.39, 62.99, 62.95, 62.48, 62.45, 15.39, 16.33, 16.12, 16.07; $^{31}$P NMR (CDCl$_3$, H$_3$PO$_4$, 161.98 MHz): δ14.92-14.62 (d, J=48.59 Hz), 11.10-10.80 (d, J=48.59 Hz); IR (CHCl$_3$): $v_{max}$ 3467, 2983, 2928, 2855, 1734, 1589, 1570, 1525, 1442, 1392, 1345, 1248, 1163, 1023 cm$^{-1}$; ESI-MS: m/z 443.94 [M+Na]$^+$; HRMS: m/z 444.0954 calcd for C$_{16}$H$_{25}$NO$_8$P$_2$+Na$^+$ (444.0947).

Example 5

Tetraisopropyl 2-(3,5-dimethoxy phenyl)ethene-1,1-diyldiphosphonate (1e)

Yellow oil; yield, 50%; $^1$H NMR (400 MHz, CDCl$_3$, ppm): δ8.24-8.05 (dd, $J_1$=32 Hz, $J_2$=48 Hz, 1H), 6.98 (s, 2H), 6.43 (s, 1H), 4.77-4.69 (m, 2H), 4.65-4.57 (m, 2H), 3.74 (s, 6H), 1.33-1.26 (m, 12H), 1.18-1.11 (m, 12H); $^{13}$C NMR (100 MHz, CDCl$_3$, ppm): δ160.26, 159.92, 108.50, 108.33, 103.36, 71.55, 71.50, 71.40, 71.35, 55.57, 24.15, 24.10, 24.07, 24.01, 23.97, 23.61, 23.57; $^{31}$P NMR (CDCl$_3$, H$_3$PO$_4$, 161.98 MHz): δ15.34-15.03 (d, J=50.21 Hz), 9.81-9.50 (d, J=50.21 Hz); IR (CHCl$_3$): $v_{max}$ 3436, 2978, 2926, 2852, 1738, 1595, 1573, 1458, 1385, 1307, 1241, 1206, 1156, 1106, 1065 cm$^{-1}$; ESI-MS: m/z 493.1 [M+1]$^+$; HRMS: m/z 493.2104 calcd for C$_{22}$H$_{39}$O$_8$P$_2$+H$^+$ (493.2114).

Example 6

Tetraisopropyl 2-(3-bromo phenyl)ethene-1,1-diyldiphosphonate (1f)

Yellow oil; yield 50%; $^1$H NMR (400 MHz, CDCl$_3$, ppm): δ8.29-8.09 (dd, $J_1$=28 Hz, $J_2$=48 Hz, 1H), 7.97 (s, 1H), 7.66 (d, J=8 Hz, 1H), 7.50 (d, J=8 Hz, 1H), 7.27-7.23 (m, 1H), 4.85-4.77 (m, 2H), 4.74-4.66 (m, 2H), 1.41-1.36 (m, 12H), 1.26-1.18 (m, 12H); $^{13}$C NMR (100 MHz, CDCl$_3$, ppm): δ157.62, 137.08, 136.94, 133.05, 132.81, 129.44, 129.00, 121.96, 71.75, 71.69, 71.54, 71.47, 29.68, 24.11, 24.06, 24.05, 24.01, 23.97, 23.92, 23.59, 23.53; $^{31}$P NMR (CDCl$_3$, H$_3$PO$_4$, 161.98 MHz): δ14.24-13.93 (d, J=50.21 Hz), 9.12-8.81 (d, J=50.21 Hz); IR (CHCl$_3$): $v_{max}$ 3436, 2978, 2930, 1581, 1385, 1242, 1105 cm$^{-1}$; ESI-MS: m/z 534 [M+Na]$^+$; HRMS: m/z 511.1003 calcd for C$_{20}$H$_{34}$BrO$_6$P$_2$+H$^+$ (511.1008).

Example 7

Tetraisopropyl 2-(3-fluoro4-methoxyphenyl)ethene-1,1-diyldiphosphonate (1g)

Yellow oil; yield 65%; $^1$H NMR (400 MHz, CDCl$_3$, ppm): δ8.18-7.98 (dd, $J_1$=28 Hz, $J_2$=48 Hz, 1H), 7.82-7.79 (m, 1H), 7.53-7.50 (d, J=12 Hz, 1H), 6.90-6.86 (m, 1H), 4.76-4.61 (m, 4H), 1.36-1.28 (m, 12H), 1.20-1.18 (m, 12H); $^{13}$C NMR (100 MHz, CDCl$_3$, ppm): δ158.28, 152.70, 150.30, 149.89, 129.36, 119.04, 118.85, 112.23, 71.54, 71.47, 71.46, 71.39, 56.20, 24.12, 24.08, 24.03, 23.99, 23.63, 23.58; $^{31}$P NMR (CDCl$_3$, H$_3$PO$_4$, 161.98 MHz): δ15.72-15.42 (d, J=48.59 Hz), 10.14-9.83 (d, J=50.21 Hz); IR (CHCl$_3$): $v_{max}$ 3436, 2978, 2928, 1668, 1615, 1511, 1443, 1385, 1285, 1138, 1105, 1017 cm$^{-1}$; ESI-MS: m/z 481 [M+1]$^+$; HRMS: m/z 481.1908 calcd for C$_{21}$H$_{36}$FO$_7$P$_2$+H$^+$ (481.1914).

Example 8

Tetraisopropyl 2-(4-N,N-dimethylamino phenyl)ethene-1,1-diyldiphosphonate (1h)

Yellow oil; yield 60%; $^1$H NMR (400 MHz, CDCl$_3$, ppm): δ8.24-8.05 (dd, J$_1$=28 Hz, J$_2$=48 Hz, 1H), 7.92-7.89 (d, J=12 Hz, 2H), 6.64 (d, J=8 Hz, 2H), 4.79-4.69 (m, 4H), 3.01 (s, 6H), 1.39-1.34 (m, 12H), 1.34-1.24 (m, 12H); $^{13}$C NMR (100 MHz, CDCl$_3$, ppm): δ160.68, 152.16, 135.0, 110.73, 71.28, 71.03, 70.99, 70.95, 39.94, 24.09, 24.05, 24.03, 23.98, 23.88, 23.65, 23.61; IR (CHCl$_3$): ν$_{max}$ 3467, 2978, 2931, 2874, 1731, 1607, 1519, 1436 1384, 1373, 1242, 1196, 1141, 1107 cm$^{-1}$; ESI-MS: m/z 476.1 [M+1]$^+$; HRMS: m/z 476.2317 calcd for C$_{22}$H$_{40}$NO$_6$P$_2$+H$^+$ (476.2325).

Example 9

Tetraisopropyl 2-(2,4,5-trimethoxy phenyl)ethene-1,1-diyldiphosphonate (1i)

Yellow oil; yield 45%; $^1$H NMR (400 MHz, CDCl$_3$, ppm): δ8.58-8.39 (dd, J$_1$=32 Hz, J$_2$=48 Hz, 1H), 7.98 (s, 1H), 6.38 (s, 1H), 4.75-4.60 (m, 4H), 3.86 (s, 3H), 3.83 (s, 3H), 3.78 (s, 3H), 1.33-1.29 (m, 12H), 1.15-1.13 (m,12H); $^{31}$P NMR (CDCl$_3$, H$_3$PO$_4$, 161.98 MHz): δ17.11-16.77 (d, J=55.07 Hz), 11.81-11.48 (d, J=53.45 Hz); IR (CHCl$_3$): ν$_{max}$ 3435, 2979, 2931, 1612, 1579, 1508, 1466, 1374, 1243, 1221, 1141 cm$^{-1}$; ESI-MS: m/z 523.1 [M+1]$^+$; HRMS: m/z 523.2222 calcd for C$_{23}$H$_{41}$O$_9$P$_2$+H$^+$ (523.2220).

Example 10

Tetraethyl 2-(naphthalen-1-yl) ethene-1,1-diyldiphosphonate (1j)

Yellow oil; yield 55%; $^1$H NMR (400 MHz, CDCl$_3$, ppm): δ8.96-8.77 (dd, J$_1$=28 Hz, J$_2$=48 Hz, 1H), 7.89-7.81 (m, 4H), 7.56-7.48 (m, 3H), 4.33-4.26 (m, 4H), 3.93-3.77 (m, 4H), 1.48-1.33 (m, 6H), 0.96-0.88 (m, 6H); $^{13}$C NMR (100 MHz, CDCl$_3$, ppm): δ160.14, 160.12, 132.95, 132.02, 130.54, 130.07, 128.61, 127.34, 126.77, 126.23, 125.05, 124.78, 124.72, 124.15, 62.88, 62.84, 62.42, 62.36, 16.42, 16.36, 15.86, 15.80; $^{31}$P NMR (CDCl$_3$, H$_3$PO$_4$, 161.98 MHz): δ16.16-15.83 (d, J=53.45 Hz), 11.81-11.48 (d, J=53.45 Hz); IR (CHCl$_3$): ν$_{max}$ 3437, 2929, 2983, 2095, 1634, 1392, 1238, 1162, 1022 cm$^{-1}$; ESI-MS: m/z 427.0 [M+Na]$^+$; HRMS: m/z 427.1430 calcd for C$_{20}$H$_{29}$O$_6$P$_2$+H$^+$ (427.1433).

Example 11

Tetra isopropyl 2-(naphthalen-1-yl)ethene-1,1-diyldiphosphonate (1k)

Yellow oil; yield 45%; $^1$HNMR (400 MHz, CDCl$_3$, ppm): δ8.85-8.67 (dd, J$_1$=28 Hz, J$_2$=48 Hz, 1H), 7.81-7.73 (m, 4H), 7.47-7.20 (m, 3H), 4.85-4.80 (m, 2H), 4.49-4.44 (m, 2H), 1.38-1.36 (m, 12H), 0.98 (d, J=8Hz, 6H), 0.88 (d, J=4Hz, 6H); $^{13}$C NMR (100 MHz, CDCl$_3$, ppm): δ158.21, 132.53, 130.38, 129.72, 129.28, 128.12, 127.12, 126.14, 125.61, 124.59, 123.86, 71.25, 71.20, 70.76, 70.71, 23.77, 23.74, 23.58, 23.53, 23.50, 22.95, 22.91; $^{31}$P NMR (CDCl$_3$, H$_3$PO$_4$, 161.98 MHz): δ14.03 13.69 (d, J=55.07 Hz), 9.66-9.33 (d, J=53.45 Hz); IR (CHCl$_3$): ν$_{max}$ 3436, 2979, 2930, 2079, 1633, 1452, 1385, 1240, 1177, 1106 cm$^{-1}$; ESI-MS: m/z 483 [M+H]$^+$; HRMS: m/z 483.2057 calcd for C$_{24}$H$_{37}$O$_6$P$_2$+H$^+$ (483.2059).

Example 12

Tetraethyl 2-(anthracene-10-yl) ethene-1,1-diyldiphosphonate (1l)

Yellow oil; yield 45%; $^1$HNMR (400 MHz, CDCl$_3$, ppm): δ8.99-8.80 (dd, J$_1$=28 Hz, J$_2$=48 Hz, 1H), 8.37 (s, 1H), 7.94-7.85 (m, 4H), 7.43-7.19 (m, 4H), 4.38-4.31 (m, 4H), 3.56-3.50 (m, 2H), 3.36-3.32 (m, 2H), 1.45-1.24 (m, 6H), 0.77-0.60 (m, 6H); $^{31}$P NMR (CDCl$_3$, H$_3$PO$_4$, 161.98 MHz): δ14.95-14.61 (d, J=55.07 Hz), 10.34-9.99 (d, J=56.69 Hz); IR (CHCl$_3$): ν$_{max}$ 3435, 2919, 1601, 1404, 1360, 1280, 1186, 1148, 1019 cm$^{-1}$; ESI-MS: m/z 477 [M+1]$^+$; HRMS: m/z 477.1590 calcd for C$_{24}$H$_{31}$O$_6$P$_2$+H$^+$ (477.1590).

Example 13

Tetraisoproyl 2-(4-nitrofuran-2-yl)ethene-1,1-diyldiphosphonate (1m)

Yellow oil; yield 45%; $^1$HNMR (400 MHz, CDCl$_3$, ppm): δ8.07-7.89 (dd, J$_1$=28 Hz, J$_2$=48 Hz, 1H), 7.85 (d, J=4 Hz, 1H), 7.35-7.34 (m, 1H), 4.83 4.76 (m, 4H), 1.40-1.32 (m, 24H); $^{13}$C NMR (100 MHz, CDCl$_3$, ppm): δ149.85, 148.62, 139.02, 124.43, 117.87, 110.35, 69.74, 69.71, 69.69, 69.67, 21.65, 21.61, 21.58, 21.55, 21.51, 21.29, 21.25; $^{31}$P NMR (CDCl$_3$, H$_3$PO$_4$, 161.98 MHz): δ12.70-12.45 (d, J=40.49 Hz), 7.62-7.37 (d, J=40.49 Hz); IR (CHCl$_3$): νmax 3436, 2980, 2928, 1591, 1530, 1454, 1386, 1351, 1247, 1142, 1104 cm$^{-1}$; ESI-MS: m/z 468 [M+1]$^+$; HRMS: m/z 468.1539 calcd for C$_{18}$H$_{32}$NO$_9$P$_2$+H$^+$ (468.1546).

Example 14

Pgp-Induction Assay

All synthesized compounds were screened for their ability to induce Pgp using rhodamine123 (Rh123) cell exclusion method. In this method, the Pgp function was evaluated in terms of rhodamine 123 (Rh123) accumulations and efflux. Briefly, the protocol used is as follows: Colorectal LS-180 cells [obtained from ECACC (European Collection of Cell Cultures) catalogue number: 87021202; passage number 52] were seeded at a density of 2×10$^4$ per well of 96 well plate and were allowed to grow for next 24 h. Cells were further incubated with the test compounds, and were diluted to a final concentration of 100 nM and rifampicin (standard) to a final concentration of 10 μM in complete media for 48 h. The final concentration of DMSO was kept at 0.1%. Drugs were removed and cells were incubated with HANKS buffer for 40 minutes before further incubation with HANKS buffer (containing 10 μM of Rh123 as a Pgp substrate) for 90 minutes. At the end of Rh123 treatment cells were washed four times with cold PBS followed by cell lysis for 1 h by using 200 μl of lysis buffer (0.1% Triton X-100 and 0.2 N NaOH). A total of 100 μl of lysate was used for reading fluorescence of Rh123 at 485 nm/529 nm. Samples were normalized by dividing fluorescence of each sample with total protein present in the lysate. For EC$_{50}$ determination, different concentrations of compound were used to treat LS180 cells for 48 h. The EC$_{50}$ value was determined by plotting fluorescence of Rh123 against concentration of compound.

The bis-phosphonate esters 1b-m showed ability to induce p-glycoprotein as showed by decrease in the % intracellular levels of rhodamine 123 in LS-180 cells (FIG. 2). One of the phosphonate ester compound 1l showed better Pgp induction activity (EC$_{50}$=0.9 nM) as compared to SR12813 (1a)

($EC_{50}$=2.04 nM). The compound 11 possesses 2-fold higher $EC_{50}$ value than SR12813 (1a). The $EC_{50}$ results are shown in Table 2.

TABLE 2

Pgp induction activity in terms of $EC_{50}$ values of 1a and 11

| Compound | Pgp induction $EC_{50}$ value |
|---|---|
| 1a | 2.04 nM |
| 11 | 0.90 nM |

Example 15

Western Blot Analysis

Protein was measured employing Bio-Rad protein assay kit using bovine serum albumin as standard. Proteins aliquots (70 μg) were resolved on SDS-PAGE and then electro transferred to PVDF membrane overnight at 4° C. at 30V. Nonspecific binding was blocked by incubation with 5% non-fat milk in Tris-buffered saline containing 0.1% Tween-20 (TBST) for 1 h at room temperature. The blots were probed with anti-Pgp antibody for 4 h and washed three times with TBST. Blot was then incubated with horseradish peroxidase conjugated antimouse secondary antibody for 1 h, washed again three times with TBST and signals detected using ECL plus chemiluminescence's kit on BioRad Chemi-Doc XRS system.

Figure 1:
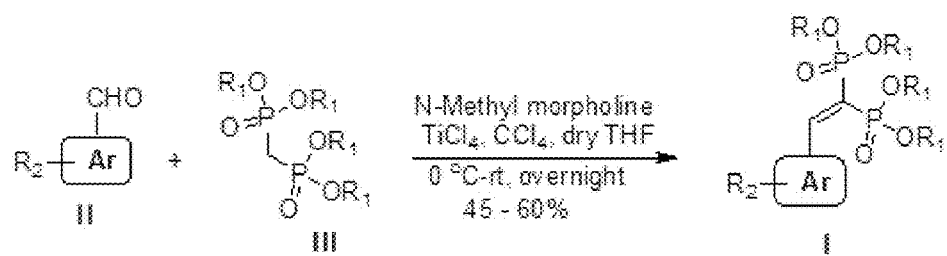
FIG. 1 is a diagram illustrating the synthetic scheme for preparation of phosphonate esters of formula I.

Upon exposure to compound 11 the p-glycoprotein mediated Rh123 efflux function in LS-180 cells is significantly increased and levels of intracellular % Rh123 is decreased as shown in FIG. 1. Furthermore in addition to that, the Western-blot results (FIG. 3) of p-glycoprotein expression clearly indicate that new phosphonate ester 11 induces p-glycoprotein expression in LS-180 cells.

Example 16

Determination of Thermodynamic Equilibrium Solubility

The compounds were first dissolved in methanol to prepare stock solutions (100 and 1000 μg/mL). Different concentrations of stock solutions were pipetted into the 96-well plates and the solvent was evaporated to ensure that solid drug was present in the beginning of the experiment. Thereafter, 200 μl of the dissolution medium (water) was added to the wells and 96-well plate was shaken horizontally at 300 rpm (Eppendorf Thermoblock Adapter, North America) for 4 h at room temperature (25±1° C.). The plates were kept overnight for equilibration of drug in medium. Later, the plates were centrifuged at 3000 rpm for 15 min (Jouan centrifuge BR4i). Supernatant (50 μl) was pipetted into UV 96-well plates (Corning® 96 Well Clear Flat Bottom UV-Transparent Microplate) for analyses with plate reader (SpectraMax Plus384) at $\lambda_{max}$ of 350 nm. The analyses were performed in triplicate for each compound. The solubility curve of concentration (ng/mL) vs absorbance was plotted to find out saturation point and the corresponding concentration was noted.

Furthermore, the phosphonate ester 11 showed optimal solubility in water as well as in other biological fluids for good in-vivo pharmacokinetics. The solubility results are shown in Table 3.

TABLE 3

Solubility of phosphonate esters 1a and 11 in water, phosphate buffer saline (PBS), simulated gastric fluid (SGF), and simulated intestinal fluid (SIF).

| | Solubility in μg/mL | | | |
|---|---|---|---|---|
| Compound | Water | PBS | SGF | SIF |
| 1a | 200 | 200 | 200 | 200 |
| 11 | 400 | >1500 | >1500 | >1500 |

ADVANTAGES OF THE INVENTION

The main advantages of the present invention are:

Compounds claimed in the present invention showed promising Pgp induction activity in LS-180 cells.

One of the compound claimed in the present invention showed Pgp induction at low nanomolar concentrations ($EC_{50}$<1 nM).

Compounds of the invention showed optimal water solubility.

Compounds of the invention are stable.

We claim:

1. A compound represented by the following structural formulae:

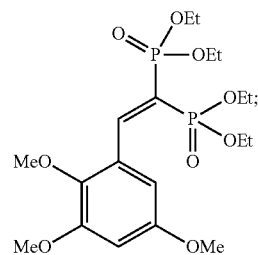

1b

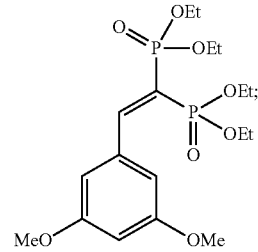

1c

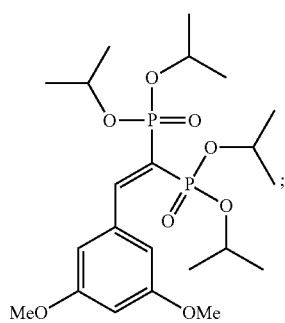

1e

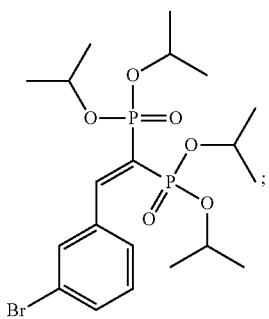 1f

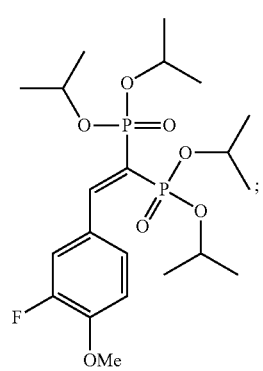 1g

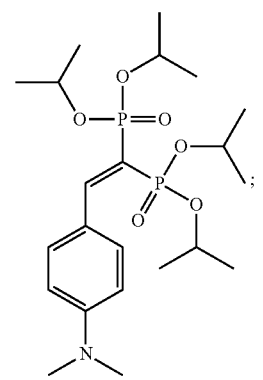 1h

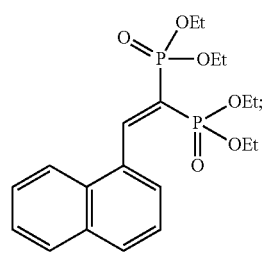 1j

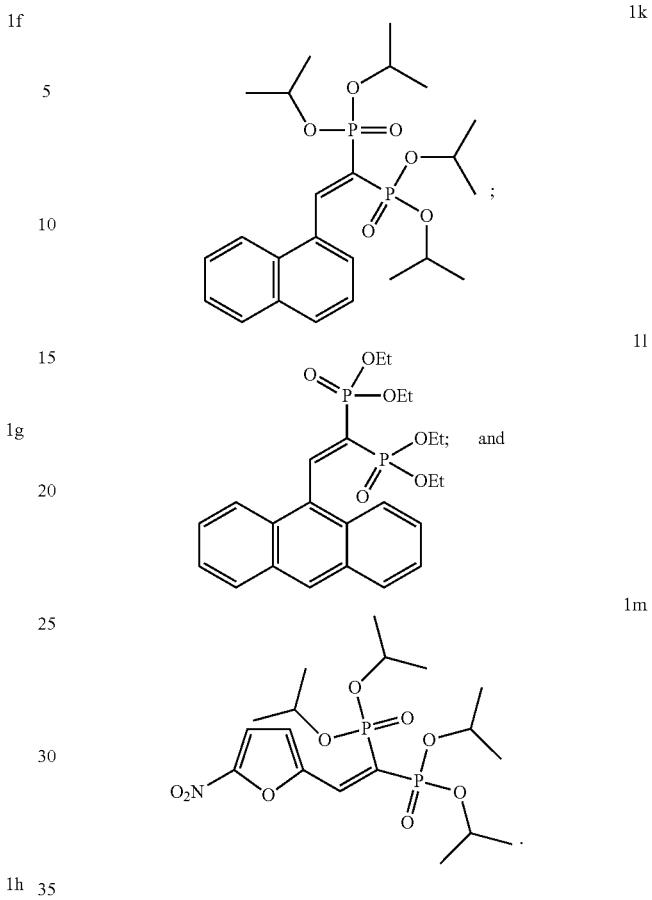

2. The compound as claimed in claim 1, wherein the said compounds are useful for the treatment of Alzheimer's disease.

3. The compound as claimed in claim 1, wherein the compound is compound 11, and the compound 11 displayed Pgp induction $EC_{50}$ value of 0.90 nM.

4. A pharmaceutical composition for the treatment of Alzheimer's disease comprising; an effective amount of the compound as claimed in claim 1 optionally along with a pharmaceutically acceptable excipients, diluents.

5. A composition as claimed in claim 4, wherein the pharmaceutically acceptable excipient is selected from a group consisting of saccharides, stearates, polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates and talc.

6. The composition as claimed in claim 5, wherein the saccharides are at least one selected from the group consisting of lactose, starch and dextrose.

7. The composition as claimed in claim 5, wherein the stearates are at least one selected from the group consisting of stearic acid and magnesium stearate.

8. The composition as claimed in claim 5, wherein the carbonates are at least one selected from the group consisting of sodium carbonate and sodium bicarbonate.

* * * * *